United States Patent [19]

D'Aoust

[11] Patent Number: 4,662,210

[45] Date of Patent: May 5, 1987

[54] MULTIPLE PARAMETER TEMPERATURE, DISSOLVED GAS AND ATMOSPHERIC PRESSURE MEASURING METHOD AND APPARATUS

[76] Inventor: Brian G. D'Aoust, 7595 Finch Rd., NE., Bainbridge Island, Wash. 98110

[21] Appl. No.: 781,116

[22] Filed: Sep. 27, 1985

[51] Int. Cl.$^4$ .............................................. G01N 7/10
[52] U.S. Cl. ...................................................... 73/19
[58] Field of Search .............. 73/19, 23, 384; 55/158, 55/270; 204/18, 406, 407, 408

[56] References Cited

U.S. PATENT DOCUMENTS

| | | | |
|---|---|---|---|
| 3,673,864 | 7/1972 | Cubberly, Jr. | 73/19 |
| 3,871,228 | 3/1975 | Weiss | 73/19 |
| 4,366,700 | 1/1983 | Bouck | 73/19 |

OTHER PUBLICATIONS

"An Automatic Dissolved Oxygen System", *Kent Tech. Rev.* (GB), No. 15, pp. 17-19, Feb. 1976.

*Primary Examiner*—Stephen A. Kreitman
*Attorney, Agent, or Firm*—George M. Cole

[57] ABSTRACT

Single, self-contained, multiple parameter device (10) and method which includes a probe (12) having a water or liquid exposed sensing compartment (61) wherein a permeable tubular membrane (46) transmits total dissolved gas pressure to a sensor (96) in a waterproof compartment. A temperature sensor (92) measures the temperature of the monitored water. Both of the sensed parameters are converted to electrical signals and routed by cable (14) to a control housing (12) and therein combined and analyzed by appropriate circuitry (100, 102, 104, 106) and with barometric pressure signals processed through a selector switch (106) to be visually read out to a display (110). The instrument (10) allows at least for selective read out and display (110) of total dissolved gas pressure, barometric pressure, temperature, percent saturation and difference between total dissolved gas and barometric pressures. Optionally, the measuring of the partial pressures of oxygen and by subtraction, approximate nitrogen can also be added to the instrument's capability.

18 Claims, 7 Drawing Figures

MULTIPLE PARAMETER TEMPERATURE, DISSOLVED GAS AND ATMOSPHERIC PRESSURE MEASURING METHOD AND APPARATUS

DESCRIPTION

1. Technical Field

The invention relates to instruments and methods techniques for measuring the total amount of gas dissolved in a liquid, solvent or solution and more particularly to a new and improved apparatus for measuring a plurality of parameters in fluids and displaying the same.

2. Background Art

The determination of total and partial gas pressures, barometric pressure and temperature provides valuable information as to the degree to which equilibrium with the gaseous environment or the atmosphere has been established. For the purpose of this discussion and description, total dissolved gas pressure in a liquid means the sum total of all partial pressures of all gasses dissolved in the liquid including the vapor pressure of the liquid. Total gas pressure, partial gas pressure, barometric pressure and temperature are information factors which are valuable in studies to determine relationships between excess pressures and environmental conditions which have created supersaturation problems. As mentioned above, fish and aquatic life in rivers, lakes, hatcheries, aquaria and other aquaculture projects have often died either of lack of oxygen from deficient saturation or of gas embolism because of the excess total pressure of dissolved gases in these various bodies of water. Such a condition facilitates bubble formation in the organisms with fatal results. As a result, instruments capable of quickly and easily providing the dissolved gas pressure information are currently used and increasingly needed to monitor waters where there is any likelihood of danger or risk to fish and aquatic life.

As those skilled in the art are aware, water in which there is as little as 10% or perhaps even less excess of dissolved gas can be stressful or lethal to fish life. Any pumped or otherwise pressurized water supply can present a risk and hence it is necessary to know the levels of air or dissolved gases in a particular system. In addition, many industries aerate or sparge water or other fluids with air or other gases to saturate with or remove air or other gases. Measuring techniques such as that herein described will facilitate economical quality control where used.

Individual instruments and techniques for measuring dissolved gas and fluid vapor pressures in solutions have for the most part been concerned with particular gaseous components. Some of the more obvious applications of a device for measuring total and partial dissolved gases are in the area of water pollution, industrial and other waste water analysis, fish hatchery water quality, aquarium water quality, and wine, beer and beverage production. There are other applications where it is desired to assess the state of gas pressure equilibrium or disequilibrium between the water or fluid and a gas phase as well as barometric pressure and temperature. Accordingly, the invention's application to water quality and atmospheric saturation is an obvious example of general applications requiring knowledge of the saturation state of any liquid with any gas phase, although an external gas phase per se is not necessary for the measurement. Clearly, these more general uses include numerous industrial and even space applications, and provide a new analytical method of greater convenience and simplicity.

Current state-of-the-art instrumentation is unnecessarily cumbersome and expensive. Because one instrument may be used for measuring a single value or property, the investment in instrumentation to measure a number of values can be prohibitive. Some of the prior non-electronic instruments, sometimes referred to as "saturometers" or "gasometers", require time consuming and tedious procedures, sometimes require water pumps and as a result present prohibitive disadvantages if a large number of measurements must be taken to monitor a relatively large body of water, or if remote measurements at depth must be made. Additionally, known "saturometers" and "gasometers" and their use require skill and training in the operators, are susceptible to damage and time consuming to repair and do not provide an absolute pressure reading but a gauge pressure which due to barometric pressure fluctuations is subject to error. Also, the use of dial gauges employing a Bourdon tube of considerable internal volume imposes further equilibration time requirements and gradual gauge errors due to corrosion. Further, the alternative of using mercury in an open-ended manometer while having the advantage of providing a true differential reading, increases the size of the devices using it and always involves environmental hazards if spilled. Such devices will require an operator or observer at the measuring site which increases the cost of measurements and decreases the utility of the devices. The above are among the more apparent disadvantages of present equipment and devices.

The existing devices for performing the measurement of total dissolved gas pressure, including the devices described in the Weiss, Bouck and D'Aoust patents listed below, have the disadvantage of requiring knowledge and experience of a specialist in making the measurements required to describe all important parameters of water quality. In addition, all previous devices require disassembly of the sensing membrane housings to accomplish a change in the membrane if it is punctured or otherwise damaged or blocked. Such prior art devices are limited in this respect by the large amount of Silicon Rubber tubing needed to overcome their internal volume. Commercially available models are also limited by the amount of silicon rubber tubing which can be interfaced with the pressure transducer and still allow ease of changing the membrane. These deficiencies are now overcome in the invention described.

It is further understood by those skilled in the art and knowledgeable in the field of fisheries from whence initial applications of these devices were forthcoming, that several different parameters are required to completely describe the saturation state iof the water or liquid being measured. The most basic of these parameters is the absolute pressure of the total dissolved gas which allows computation of the other parameters provided the instrument is used in a certain sequential manner. Prior art does not provide for these measurements simultaneously in one instrument.

A problem in comparing measurements taken with prior art is the lack of an accurate reading of barometric pressure while taking the measurement. This is particularly critical when the dissolved gas measurement is described as "% saturation", since this notation does not record either the absolute dissolved gas pressure or the barometric pressure at the site of observation. When this information is omitted, large errors can result from measurements of the same dissolved gas pressure at different altitudes.

On the other hand, a measurement of dissolved gas pressure relative to barometric pressure at the water surface while giving a value for "Delta-P" as given by Weiss and Bouck also ignores the absolute value of the barometric pressure, and therefore prevents expressing the degree of saturation as "percent saturation" which remains a popular industry standard.

It will be obvious that the only way to overcome these difficulties is to provide simultaneous measurements and readings of all three parameters which is accomplished in the instant invention herein described and claimed.

Incorporated by reference herein is the subject matter of applicant's co-pending application Ser. No. 634,147, filed July 24, 1984 for "Total Dissolved Gas Pressure Measuring Device", now U.S. Pat. No. 4,563,892.

Among the known prior art publications relating to this subject matter are the following U.S. Letters Pat. Nos.:

U.S. Pat. No. 3,438,241 is a structurally unrelated device which is directed toward selected gas pressure measurement as opposed to total dissolved gas pressure.

U.S. Pat. No. 3,871,228 is directed to a device for total pressure measurement but structurally and functionally is significantly different from that of the instant application.

U.S. Pat. No. 4,366,700 also measures total dissolved gas dissolved in a fluid but again is also structurally significantly different from the instant device.

U.S. Pat. Nos. 3,668,837 and 3,673,864 are of interest only and significantly unrelated to the specifics of the instant invention.

DISCLOSURE OF THE INVENTION

The instant invention is a single instrument device and method which includes a probe with an absolute pressure sensor which is connected to a gas phase formed in this case by thin walled gas permeable tubing. In the same probe component is incorporated a thermometer for measuring temperature of the liquid being monitored, thereby allowing computations of the potential content of different gases. In addition, the instrument includes an electronic barometer within the control housing. Power and sensing circuitry are included with circuitry for analyzing, integrating, displaying and outputting a minimum of five values, namely total dissolved gas pressure, barometric pressure, the ratio of the total dissolved gas pressure and barometric pressure (percent saturation) and the difference between the total dissolved gas and barometric pressure. The probe is a cylindrical member including one waterproof chamber in which is housed the gas pressure and temperature sensors and an open compartment through which the water measured freely circulates and contacts both the gas permeable membrane and the thermally connected temperature sensor housing. Pressure and temperature signals obtained in this way are relayed through the cable to the control box for display and readout.

Accordingly, it is among the many features of the instant invention that it combines in one instrument the capability of sensing and measuring several basic values and enabling the operator to obtain at least give related values or parameters which can be displayed and read by an operator by simple use of a selector knob or switch on the instrument. The device is accurate and includes interchangeable modular parts for simple and rapid repair and replacement of individual components or assemblies of parts. The instrument is compact, small and position-insensitive and can be used at the site of the liquid to be measured or the body of water to be monitored. It is less complicated to operate than known devices and easily maintained. The device holds the internal gas phase volume to a minimum so thae time for obtaining a measurement is greatly reduced.

BEST MODE FOR CARRYING OUT THE INVENTION

Figure 1:
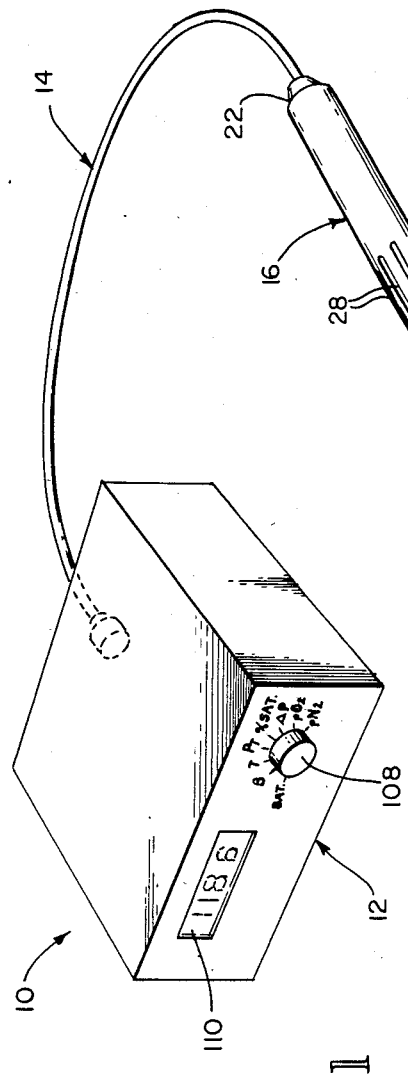
FIG. 1 is a general view in perspective of how the instrument with selector knob and display readout together with the probe component will appear.

Referring now to the drawings, it will be seen in FIG. 1 that the instrument generally designated by the number 10, is composed of control chassis or housing 12, waterproof cable and connector 14 and probe 16, the details of which will now be described in detail.

Probe 16 includes elongated cylindrical housing 18 which has front end 20 and rear end 22. Front end 20 is partially closed by a threaded opening 24 of reduced diameter while the rear or back end 22 is completely open. The body or cylindrical housing 18 has inner surface 26 extending from the partially closed front end 20 to the open rear end 22. A predetermined number of longitudinally elongate openings 28 are located circumferentially around the body of the housing 18 so that the liquid or water to be monitored can freely flow in through the front end 20 and through the openings 28 in the side wall. Note that the openings are in approximately the front half of housing 16.

Figure 2:
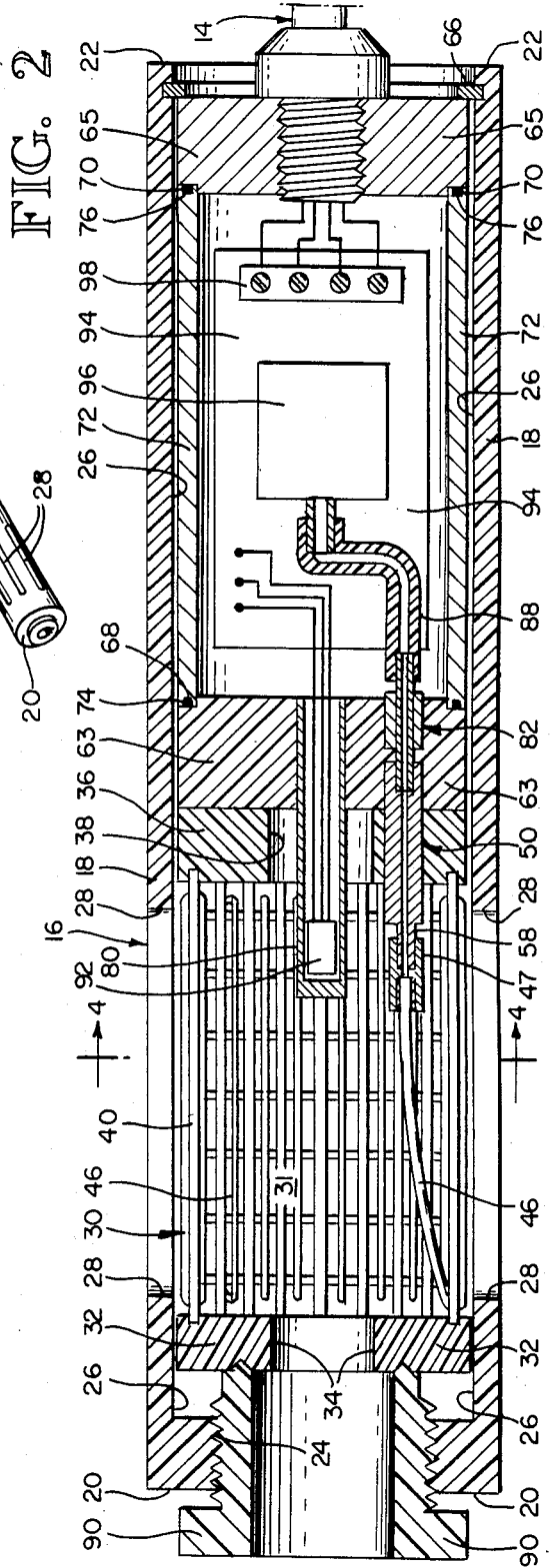
FIG. 2 is an elevational cross-section view of the probe taken longitudinally and showing detais of construction thereof.
Figure 3:
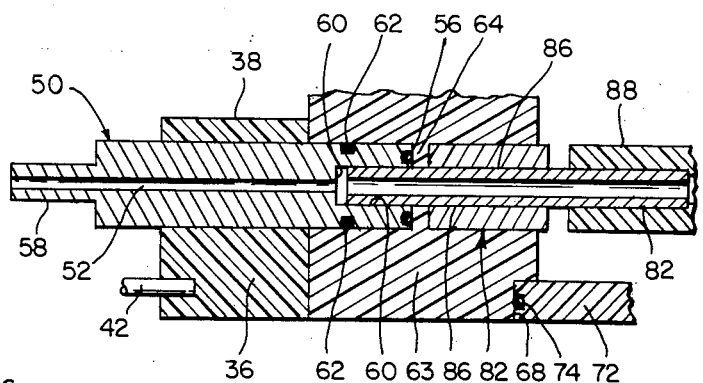
FIG. 3 is a transverse cross-section view along the line 3—3 of FIG. 2 showing additional details of construction of the sensing compartment of the probe.

The element responsible for providing the small gas phase for pressure sensing of the total dissolved gas pressure is the membrane cartridge generally designated by the number 30 and including thick front end disk member 32 which occupies substantially the entire inside diameter of housing 18 with free clearance. Disk 32 is provided with through way opening 34 and is also provided with an annular groove on its inside surface near its outer edge as is best seen in FIG. 2. In like manner, a thick rear support disk 36 for the cartridge 30 also occupies substantially the entire inner diameter of the housing but with free clearance from inside housing surface 26, and is also provided with central opening 38. The grid member 40 is a plastic screen or grid made up of a plurality of spaced apart and generally parallel longitudinal bars 42 and a series of spaced connector bars 44 generally at right angles thereto. The opposed ends of the screen or grid fit into the opposed faces of disks 32 and 36 by fitting into the facing annular grooves as is best shown in FIG. 2. The cylindrical grid or screen 40 is the support for tubing 46 which is made of silicon rubber or other material of satisfactory gas permeable characteristics. While silicon rubber tubing 46 is used any other hydrostatically insensitive means for forming an exchangeable gas phase may also be employed. In this regard see applicant's U.S. Pat. No. 4,563,892 referred to above. Tubing 46 is a single continuous permeable membrane which is closed at its outer end and which connects to impermeable tubing as will be described hereinafter. A predetermined length of the tubing is wound around the grid or screen 40 support. The screen 40 can also be found as extruded polypropylene well-screen tubes of appropriate diameter.

Figure 4:
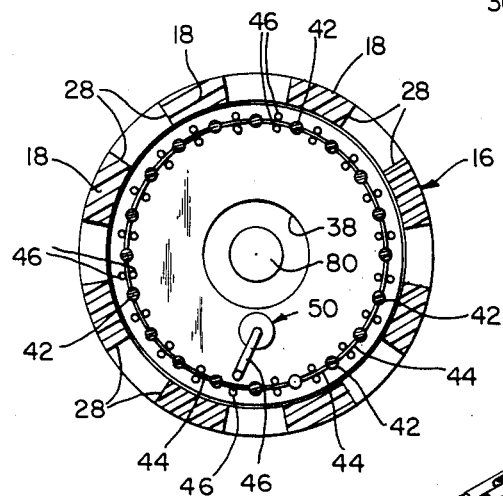
FIG. 4 is an enlarged partial cross-section view of the central portion of the probe illustrating additional detils of construction thereof.
Figure 5:
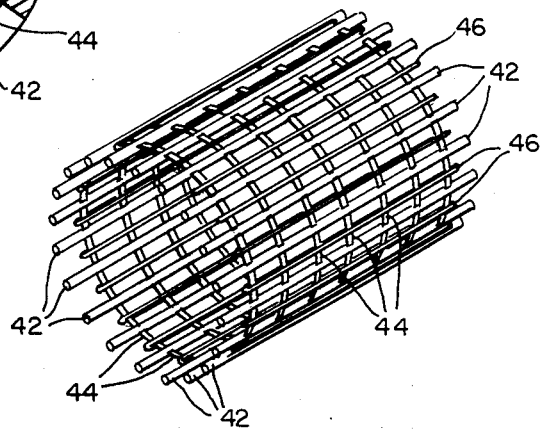
FIG. 5 is a general view in perspective of the cylindrical grid or carrier device for the permeable tubing which functions as the dissolved gas sensing portion of the probe.
Figure 6:
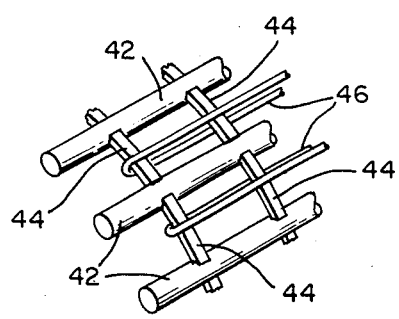
FIG. 6 is an enlarged partial view of a portion of FIG. 5 showing more specifically details of the construction of the manner in which the permeable tubing is mounted in the probe.

Firmly mounted in the body of donut-shaped disk 36 is a tubular fitting generally designated by the number 50 as can best be seen in FIG. 4. Fitting 50 is an elongated stainless steel member with tubular passage 52 running centrally therethrough from its front end 54 to its inner end 56. It will be noted that fitting 50 is necked down at the front thereof as at 58 for the purpose of receiving the end of permeable tubing 46 or adapter 47. Tubular passage 52 (FIG. 4) extends to the back end 56 where a recessed portion define an enlarged tubular cavity or recess 60 into which passage 52 opens. The recess 60 is of somewhat larger diameter than the tubular passage 52 as can be seen in FIG. 4. It should also be noted that an O-ring 62 is provided in the circumferential wall near the back end 56 and that an O-ring 64 is provided in the end surface 56 as shown and for the purposes which will be described hereinafter. Again fitting 50 while preferably made of stainless steel can also be made of brass or perhaps other materials. It is pressed fit into donut-shaped disk 36. An adapter 47 is designed to receive the end of permeable tube 46 and to connect the tube 46 to end 58 of fitting 50.

A waterproof chamber 61 is disposed in the rear portion of housing 16 between forward disk 63 and rear disk 65 and wherein disk 65 is held in place by the expander retaining ring 66 located in close proximity to housing rear end 22. Each of the waterproof chamber 60 disks 63 and 65 is provided with an annular offset surface 68 on forward disk 63 and offset surface 70 on rear disk 65. A plastic tubular housing 72 completes the waterproof chamber 61 and is provided with annular facing grooves to accommodate O-ring 74 at one end and O-ring 76 at the opposite end.

Extending forwardly from front disk 63 through opening 38 and into chamber 31 is a closed stainless steel temperature sensor housing or tube 80 which is generally centrally located of disk 63 and pressed-fit, bonded or otherwise connected so as to establish a waterproof connection between disk 63 and temperature tube 80. The front disk 63 of the waterproof compartment portion of the housing also includes a recess 84 on its front face for receiving the rearward section of fitting 50. A fitting 82 also is made of stainless steel or brass and contains tube 86 which extends forwardly through disk 63 and into recess 60 at the rear portion of fitting 50. Tube 86 also extends rearwardly into chamber 61 to receive one end of flexible gas connector or adapter 88. It will be appreciated that the membrane cartridge at the forward portion of the housing and the waterproof chamber in the rear half of the housing are held in place by the snap ring 66 at the rear end and by retainer screw or equivalent 90 at the front end which is received in the threaded opening 24 which at its inner end applies pressure to disk 32. The O-rings on the front and rear face of the interior housing 72 for the waterproof compartment are thus made effective against the annular offset surfaces 68 and 70 of discs 63 and 65.

The thermometer or temperature sensor 92 in temperature tube 80 is connected to circuit board 94 which also supports a piezo electric strain gauge 96 to which flexible adapter or connector 88 is connected. Appropriate electrical connections for power and signal are made from broad 94 via cable 14 to the control chassis or housing 12.

It will be appreciated that the sensor 96 which is in the form of a piezo electric strain gauge reacts to the gas pressure established by diffusion of dissolved gases through membrane 46, tubular passage 52, tube 86 and connector 88 to output an electrical pressure signal through the cable 14. In like manner, the temperature sensor 92 through circuit board 94 outputs an electrical signal via terminal block 98 and cable 14 to the control housing 12. Circuit board 94 carries the necessary voltage regulators, resistors and other electrical components necessary to provide constant voltage or current to the respective sensors regardless of cable length allowing cable extensions to be applied with no need fr recalibration. The structure of probe 16 facilitates ease of replacement of the parts as well as whole assemblies if desired or needed. Thus, the user has an option of replacing any component or entire assemblies easily and conveniently.

Figure 7:
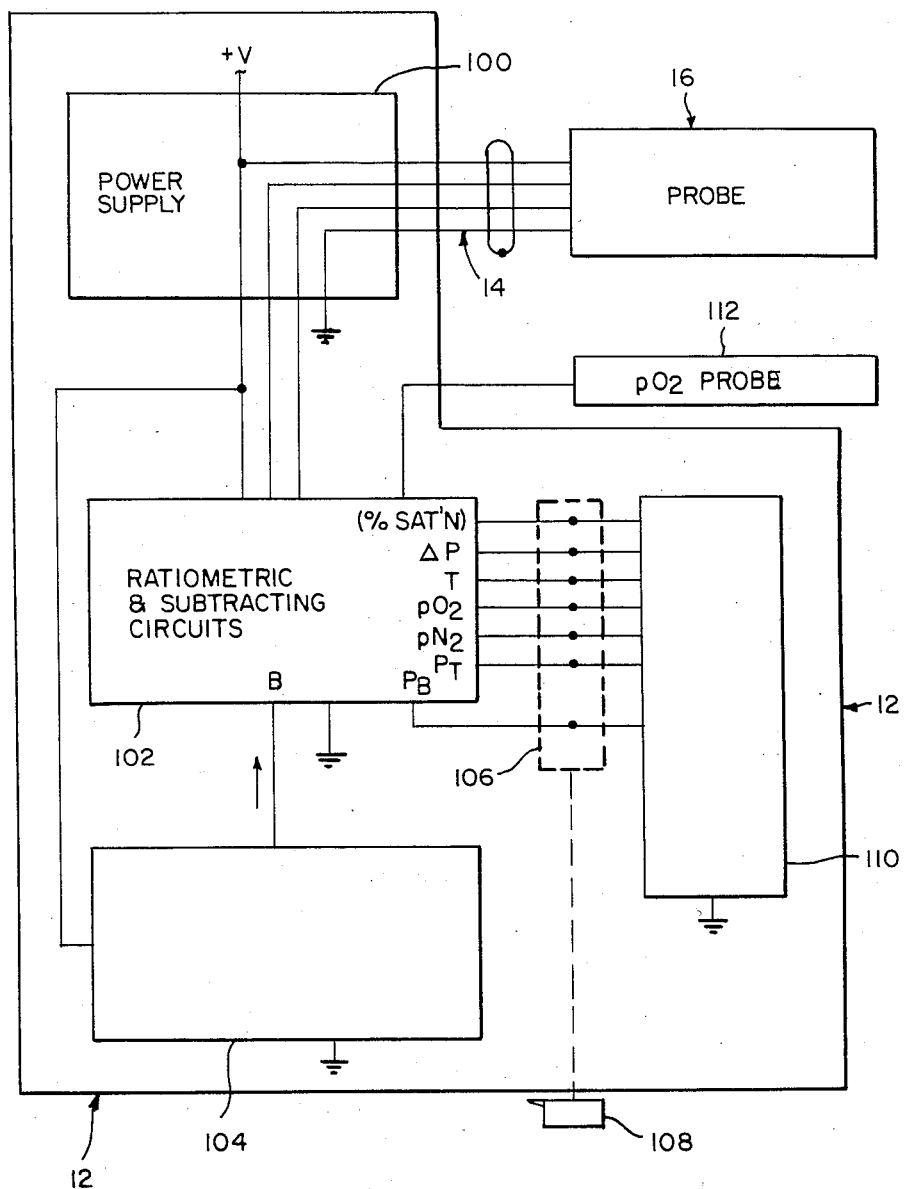
FIG. 7 is a diagrammatic view showing the functional portions of the electronic circuitry of the control box.

Referring now to FIG. 7, it will be seen that the heavy line represents the chassis or control housing 12 with cable 14 extending from probe 16. The control box contains power supply 100, analyzer circuitry 102, electronic barometer 104, selector switch 106 which is controlled by control knob 108 and display or readout 110. A partial pressure oxygen probe 112 may also be connected to provide electrical inputs to the analyzer circuitry 102 as is shown in this figure. Reference to the analyzer circuit 102 includes as parts thereof components which sense signal conditions and variously combine the sensor inputs to provide the scaled readout of the various parameters. Again, the parameters which can be selected by simple turning of the selector knob 108 to actuate selector switch 106 provides a digital readout of total dissolved gas pressure, barometric pressure, temperature, percent saturation, the difference in the dissolved gas and barometric pressures, or as is sometimes referred to in the industry "Delta-P" ($\Delta$ P) and optionally, if an oxygen sensor is provided, a readout of the partial pressure of oxygen $pO_2$.

The present invention combines in one instrument what a number of different sensor instruments were formerly utilized to provide. For instance, in other instruments partial pressures will be provided in terms of millimeters of mercury and barometric pressure in millibars or inches of mercury. Oxygen content is usually expressed as parts per million but in this instrument is displayed as a partial pressure ($pO_2$) allowing subtraction and display of an approximate nitrogen $pN_2$ parameter. In this instrument, these parameters or values are thus combined in a consistent form using a unique combination of sensors to provide through analog circuitry a single, self-contained, multiple parameter instrument which can provide all of the information which is critical to water quality monitoring. In addition, the availability of analog output of the different parameters allows interfacing with chart recorders or any computer equipment having analog-to-digital conversion capability. Thus, the versatility of the instrument for field work or continuous monitoring is maximized and it can operate automatically at great saving in operator time.

I claim:

1. A method for single instrument provision of multiple parameter monitoring information for water and liquid quality, comprising the steps of:
    (a) sensing temperature of the body of water or liquid being monitored,
    (b) sensing the total dissolved gas pressure of said water or liquid,
    (c) sensing the barometric pressure,
    (d) converting the sensed temperature, total dissolved gas pressure and barometric pressure to electronic analog signals,
    (e) directing said electronic analog signals to an analyzer circuit to enable said analyzer circuit to provide separate output signals of at least the following parameters, namely: total dissolved gas pressure, temperature, barometric pressure, percent saturation and difference between total dissolved gas and barometric pressures, and
    (f) selectively directing each separate output signal from said analyzer circuit via a selector circuit to a visual display and readout means.

2. The method according to claim 1 and wherein the partial pressure of dissolved oxygen in said body of liquid or water is also sensed, converted to electronic signals and selectively displayed on said read out means, and as another parameter, subtracted from the total dissolved gas pressure to provide a measure of the remaining gases present, which in airequilibrated water very closely approximates nitrogen and argon when corrected for water vapor.

3. A single instrument water and liquid quality monitoring device, comprising:
    (a) a probe means including a housing having an open first sensing compartment and into and through which said water or liquid is circulated, said first compartment including means for sensing temperature and means for sensing total dissolved gas pressure, said probe also containing a waterproof second sensor compartment including means for receiving and converting said sensed temperature and total dissolved gas pressure into electronic signals,
    (b) a control housing containing electronic components for providing electrical power and including a circuit means for receiving said electronic signals from said probe means, and further including means for measuring barometric pressure and directing an electronic signal representing said barometric pressure to said circuit means, wherein said circuit means is adapted to provide at least output signals representing total dissolved gas pressure, temperature, barometric pressure, percent saturation and the difference between total dissolved gas and barometric pressures, said control housing further containing selector switch means for receiving said output signals from said circuit means and also including display means for visually reading out each said signal selectively directed thereto from said selector circuit, and
    (c) cable means interconnecting said probe with said control housing.

4. The water and liquid quality monitoring device according to claim 3 and wherein said probe means is an elongated cylindrical housing having front and rear ends, said housing containing said first compartment generally in the front portion thereof and said second compartment in the rear portion thereof.

5. The water and liquid quality monitoring device according to claim 3 and in which said means for sensing total dissolved gas pressure is a gas permeable membrane tubing of predetermined length.

6. The water and liquid quality monitoring device according to claim 3 and wherein gas impermeable tubing in said probe connects to the gas permeable tubing of said first compartment and also connects to sensor means in said second compartment for converting total dissolved gas pressure to an electronic signal output.

7. The water and liquid quality monitoring device according to claim 3 and wherein said first and second compartments are defined by separable parts within said probe housing such that said parts may be removed from said housing for easy repair and replacement.

8. The water and liquid quality monitoring device according to claim 4 and in which said means for sensing total dissolved gas pressure is a gas permeable membrane tubing of predetermined length.

9. The water and liquid quality monitoring device according to claim 8 and wherein gas impermeable tubing in said probe connects to the gas permeable tubing of said first compartment and also connects to sensor means in said second compartment for converting total dissolved gas pressure to an electronic signal output.

10. The water and liquid quality monitoring device according to claim 9 and wherein said first and second compartments are defined by separable parts within said probe housing such that said parts may be removed from said housing for easy repair and replacement.

11. A single instrument water and liquid quality monitoring device, comprising:
    (a) a probe means including a housing having an open first sensing compartment and into and through which said water or liquid is circulated, said first compartment including means for sensing temperature and means for sensing total dissolved gas pressure, said probe also containing a waterproof second sensor compartment including means for receiving and converting said sensed temperature and total dissolved gas pressure into separate electronic signals,
    (b) a control housing containing electronic components for providing electrical power and including an analyzer circuit for receiving said separatel electronic signals from said probe means, and further including means for measuring barometric pressure and directing an electronic signal representing said barometric pressure to said analyzer circuit, wherein said analyzer circuit is adapted to provide at least separate parameter output signals representing total dissolved gas pressure, temperature, barometric pressure, percent saturation and the difference between total dissolved gas and barometric pressures, said control housing further containing selector switch means for receiving said separate output sgnals from said analyzer circuit and also including display means for visually reading out each said separate parameter signal selectively directed thereto from said selector circuit, and (c) cable means interconnecting the second sensor compartment of said probe with said control housing.

12. The water and liquid quality monitoring device according to claim 11 and wherein said probe means is an elongated cylindrical housing having front and rear ends, said housing containing said first compartment generally in the front portion thereof and said second compartment in the rear portion thereof.

13. The water and liquid quality monitoring device according to claim 11 and in which said means for sensing total dissolved gas pressure is a gas permeable membrane tubing of predetermined length.

14. The water and liquid quality monitoring device according to claim 11 and wherein said impermeable tubing in said probe connects to the gas permeable tubing of said first compartment and also connects to sensor means in said second compartment for converting total dissolved gas pressure to an electronic signal output.

15. The water and liquid qualtiy monitoring device according to claim 11 and wherein said first and second compartments are defined by separable parts within said probe housing such that said parts may be removed from said housing for easy repair and replacement.

16. The water and liquid quality monitoring device according to claim 12 and in which said means for sensing total dissolved gas pressure is a gas permeable membrane tubing of predetermined length.

17. The water and liquid quality monitoring device according to claim 16 and wherein said impermeable tubing in said probe connects to the gas permeble tubing of said first compartment and also connects to sensor means in said second compartment for converting total dissolved gas pressure to an electronic signal output.

18. The water and liquid quality monitoring device according to claim 17 and wherein said first and second compartments are defined by separable parts within said probe housing such that said parts may be removed from said housing for easy repair and replacement.

* * * * *